(12) United States Patent
Huang et al.

(10) Patent No.: US 6,974,589 B1
(45) Date of Patent: Dec. 13, 2005

(54) NEUTRAL-CATIONIC LIPID FOR NUCLEIC ACID AND DRUG DELIVERY

(75) Inventors: Shi Kun Huang, Castro Valley, CA (US); Samuel Zalipsky, Redwood City, CA (US); Wei-Ming Zhang, San Francisco, CA (US); Bei Jin, Union City, CA (US); Yolanda P. Quinn, Daly City, CA (US)

(73) Assignee: Miza Corporation, Mountain View, CA (US)

( * ) Notice: Subject to any disclaimer, the term of this patent is extended or adjusted under 35 U.S.C. 154(b) by 0 days.

(21) Appl. No.: 09/685,940

(22) Filed: Oct. 10, 2000

Related U.S. Application Data (63) Continuation of application No. 09/680,614, filed on Oct. 6, 2000.

(60) Provisional application No. 60/158,693, filed on Oct. 8, 1999.

(51) Int. Cl.[7] .............................................. A61K 9/127
(52) U.S. Cl. .................. 424/450; 424/1.21; 424/9.321; 424/9.51; 424/417; 428/402.2
(58) Field of Search ............................... 424/450, 1.21, 424/9.321, 9.51, 417, 94.3; 436/829; 935/54; 428/402.2

(56) References Cited

U.S. PATENT DOCUMENTS

| | | | |
|---|---|---|---|
| 5,013,556 A | 5/1991 | Woodle et al. | |
| 5,395,619 A | 3/1995 | Zalipsky et al. | |
| 5,631,018 A | 5/1997 | Zalipsky et al. | |
| 5,891,468 A | 4/1999 | Martin et al. | |
| 5,965,434 A | 10/1999 | Wolff et al. | |
| 6,056,973 A | * 5/2000 | Allen | |

FOREIGN PATENT DOCUMENTS

| | | |
|---|---|---|
| WO | WO97/00241 | 1/1997 |
| WO | WO97/07784 A2 | 3/1997 |
| WO | WO00/30444 | 6/2000 |
| WO | WO01/26625 | 4/2001 |

OTHER PUBLICATIONS

Conner et al., "," Proc. Nat'l. Acad. Sci. (USA), p. 1715, (Jun. 28, 1984).

Chu and Szoka, "J. Liposome Res.," vol. 4 (No. 1), p. 361, (Jun. 28, 1994).

(Continued)

Primary Examiner—Gollamudi S. Kishore

(57) ABSTRACT

A lipid represented by the formula:

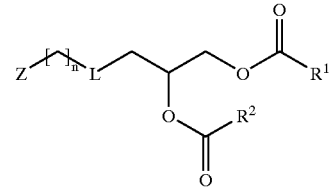

wherein each of $R^1$ and $R^2$ is an alkyl or alkenyl chain having between about 8 to about 24 carbon atoms; n=0–20; L is selected from the group consisting of (i) —X—(C=O)—Y—, (ii) —X—(C=O)—, and (iii) —X—CH$_2$—, wherein X and Y are independently selected from oxygen, NH, and a direct bond; and Z is a weakly basic moiety that has a pK of less than about 7.4 and greater than about 4.0 is described.

22 Claims, 7 Drawing Sheets

OTHER PUBLICATIONS

Szoke et al., ",". Ann. Rev. Biophys. Bioeng., p. 467, (Jun. 28, 1980).

Zalipsky, S., "Stealth Liposomes, Chapter 9," CRC Press, (Jun. 28, 1995).

Allen, T.M. et al., ",". Biochemica et Biophysica Acta, p. 99-108, (Jun. 28, 1995).

Zalipsky, S., ",". Bioconjugate Chem., vol. 4 (No. 4), p. 296-299, (Jun. 28, 1993).

Zalipsky, S. et al., ",". FEB Lett., p. 71-74, (Jun. 28, 1994).

Zalipsky, S. et al., ",". Bioconjugate Chem., p. 705-708, (Jun. 28, 1995).

Martin, F. J., "Specialized Drug Del. Systems-Manuf. & Prod. Tech.," p. 267-316, (Jun. 28, 1990).

Xu and Szoka, ",". Biochemistry, p. 5616-5623, (Jun. 28, 1996).

* cited by examiner

NEUTRAL-CATIONIC LIPID FOR NUCLEIC ACID AND DRUG DELIVERY

CROSS-REFERENCE TO RELATED APPLICATIONS

This application is a continuation of U.S. application Ser. No. 09/680,614, filed Oct. 6, 2000, which claims the benefit of U.S. application No. 60/158,693, filed Oct. 8, 1999. Both documents are incorporated by reference herein.

FIELD OF THE INVENTION

The present invention relates to a lipid having a moiety that is responsive to pH such that the lipid is essentially neutral at physiologic pH, and has a predominantly positive charge at a pH lower than physiologic pH. The invention also relates to a liposome composition prepared with the lipid.

BACKGROUND OF THE INVENTION

The transmission of biologically active materials to cells is an essential component of a wide range of therapies. Such therapies include supplying a cell with a protein having a necessary biological activity, providing a nucleic acid (i.e., DNA, RNA, cDNA) molecule to a cell (gene therapy), immunizing a subject against a foreign protein (vaccination), immunizing a subject against a foreign protein by introducing a gene that encodes for the protein (gene vaccination), and inhibiting the production of a protein in a cell by providing the cell with a nucleic acid molecule that is antisense i.e., complimentary, to mRNA encoding the protein or otherwise interfering with the mRNA encoding the protein.

There are, however, several obstacles to delivery of such agents to a cell, including the fact that the phospholipid bilayer containing the outer membrane of most cells prohibits indiscriminate entry of materials into the cell. Approaches described to introduce active agents into cells include, for example, microinjection and electroporation. Other approaches involve viral vectors and chemical-mediated introduction.

Another approach for delivery of active agents to cells, described in the art, is liposome-based delivery. In particular, delivery of genetic material to cells using liposomes has been widely studied. It is generally understood that liposome vesicles are taken up by cells via endocytosis and enter the lysosomal degradation pathway. Thus, some effort towards designing liposomes that avoid degradation has been made. One approach has been to include in the liposome a pH sensitive lipid, such as palmitoylhomocysteine (Connor et al., *Proc. Natl. Acad. Sci.* (USA) 81:1715 (1984); Chu and Szoka, *J. Liposome Res.*, 4(1):361 (1994)). Such pH sensitive lipids at neutral pH are negatively charged and are stably incorporated into the liposome lipid bilayers. However, at weakly acidic pH (pH less than about 6.8) the lipid becomes neutral in charge and changes in structure sufficiently to destabilize the liposome bilayers. The lipid, when incorporated into a liposome that has been taken into an endosome, where the pH is reported to be between about 5.0 to about 6.0, destabilizes and causes a release of the liposome contents.

The use of cationic lipids, e.g., derivatives of glycolipids with a positively charged ammonium or sulfonium ion-containing headgroup, for delivery of negatively-charged biomolecules, such as oligonucleotides and gene fragments, as a liposome lipid bilayer component is also widely reported. The positively-charged headgroup of the lipid interacts with the negatively-charged cell surface, facilitating contact and delivery of the biomolecule to the cell.

Despite these efforts, delivery of biomolecules, such as oligonucleotides and other materials, as described above, to cells is still lacking in the art. The present invention provides compositions and methods for improving the transfer of an agent, such as a nucleic acid, to cells.

SUMMARY OF THE INVENTION

The invention provides a liposome composition for delivery of an agent to a cell.

The invention further provides a lipid for use in a liposome composition for delivery of an agent to a cell.

In one aspect, the invention includes a liposome composition containing a lipid represented by the formula:

wherein each of $R^1$ and $R^2$ is an alkyl or alkenyl chain having between about 8 to about 24 carbon atoms; n=0–20; L is selected from the group consisting of (I) —X—(C=O)—Y—, (ii) —X—(C=O)—, and (iii) —X—CH$_2$—, wherein X and Y are independently selected from oxygen, NH, and a direct bond; and Z is a weakly basic moiety that has a pK of less than about 7.4 and greater than about 4.0.

In one specific embodiment, X is NH and Y is oxygen. In other embodiments, L is a carbamate linkage (NH—(C=O)—O—CH$_2$), an ester linkage or a carbonate linkage. In a preferred embodiment, Z is an imidazole. Preferably, $R^1$ and $R^2$ is an unbranched alkyl or alkenyl chain having between about 8 to about 24 carbon atoms, and in a preferred embodiment, $R^1$ and $R^2$ are each stearyl groups ($C_{17}H_{35}$). In another preferred embodiment, n is between 1–10.

The liposomes, in one embodiment, include between about 1 to about 80 mole percent of the lipid having the formula shown above.

In another embodiment, Z is a moiety having a pK value between about 5.0 to about 6.5.

The liposomes having the lipid represented by the formula above, in a preferred embodiment, include a therapeutic compound entrapped in the liposomes. In one embodiment, the therapeutic agent is a nucleic acid, such as DNA, RNA, or fragments thereof. The liposomes can also include a ligand for targeting the liposomes to a target site, such as a ligand having binding affinity for endothelial tumor cells and which is internalized by such cells, such as E-selectin, Her-2 and FGF.

In another embodiment, the liposomes include between about 5 to about 20 mole percent of a vesicle-forming lipid derivatized with a hydrophilic polymer chain. The hydrophilic polymer chain in a preferred embodiment is polyethyleneglycol (PEG).

BRIEF DESCRIPTION OF THE DRAWINGS

FIG. 6A shows the transfected cells viewed under fluorescence microscopy and FIG. 6B shows the transfected cells viewed under light microscopy. FIGS. 6C–6D are micrographs of the cells after transfection with similar liposomes which do not have the targeting antibody, where the cells after incubation with the liposomes are shown under fluorescence microscopy in FIG. 6C and under light microscopy in FIG. 6D.

DETAILED DESCRIPTION OF THE INVENTION

I. In describing the present invention, the following terminology will be used in accordance with the definitions set out below.

"Nucleic acid" as used herein, refers to a linear polymeric form of nucleotides of any length, either ribonucleotides or deoxynucleotides, and includes both double- and single-stranded DNA and RNA. A nucleic acid may include both coding and noncoding regions that can be obtained directly from a natural source (e.g., a microorganism), or can be prepared with the aid of recombinant or synthetic techniques. A nucleic acid molecule may be equivalent to a nucleic acid fragment or it can be a nucleic acid fragment in addition to one or more other nucleotides, oligonucleotides, or polynucleotides. For example, the nucleic acid molecule of the invention can be a vector or plasmid such as an expression or cloning vector or plasmid.

As used herein, a "neutral" lipid is one that is uncharged, i.e., having no ionic character.

A "charged" lipid is one having a positive or negative charge, i.e., having ionic character.

A "Vesicle-forming lipid" refers to an amphipathic lipid containing hydrophobic and polar head group moieties, which can form spontaneously into a bilayer vesicle in water, as exemplified by a phospholipid, or is stably incorporated into lipid bilayers, with the hydrophobic moiety in contact with the interior hydrophobic region of the bilayer membrane, and the polar head group moiety oriented toward the exterior polar surface of the membrane. The vesicle-forming lipid of this type typically includes one or two hydrophobic acyl hydrocarbon chains or a steroid group, and may contain a chemically reactive group, such as an amine, acid, ester, aldehyde or alcohol, at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14 to about 22 carbon atoms in length, and have varying degrees of unsaturation. Also included within the scope of the term "vesicle-forming lipid" is a glycolipid, such as a cerebroside and a ganglioside, and a sterol, such as cholesterol.

"Alkyl" refers to a fully saturated monovalent radical containing carbon and hydrogen, which may be branched or a straight chain. Examples of alkyl groups are methyl, ethyl, n-butyl, t-butyl, n-heptyl, and isopropyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to a monovalent radical containing carbon and hydrogen, which may be branched or a straight chain, containing one or more double bonds.

Abbreviations: PEG: polyethylene glycol; mPEG: methoxy-terminated polyethylene glycol; Chol: cholesterol; PC: phosphatidyl choline; PHPC: partially hydrogenated phosphatidyl choline; PHEPC: partially hydrogenated egg phosphatidyl choline; HSPC: hydrogenated soy phosphatidyl choline; DSPE: distearoyl phosphatidyl ethanolamine; APD: 1-amino-2,3-propanediol; DTPA: diethylenetetramine pentaacetic acid; Bn: benzyl.

II. Cationic-Neutral Lipid

In one aspect, the invention includes lipids represented by the structure shown below:

wherein each of $R^1$ and $R^2$ is an alkyl or alkenyl chain having between about 8 to about 24 carbon atoms; n=0–20; and in a preferred embodiment is between 1–10; L is selected from the group consisting of (i) —X—(C=O)—Y—, (ii) —X—(C=O)—, and (iii) —X—CH$_2$—, wherein X and Y are independently selected from oxygen, NH, and a direct bond; and Z is a weakly basic moiety that has a pK of less than about 7.4 and greater than about 4.0.

The weakly basic moiety Z results in a lipid that at physiologic pH of about 7.4 is predominantly, for example, in an amount of at least 50%, neutral in charge but at a selected or specified pH, has a value less than physiologic pH and tends to a positive charge. For example, in one embodiment, Z is an imidazole moiety, which has a pK of about 6.0. At physiologic pH 7.4, this moiety is predominantly neutral, but at pH values of less than 6.0, the moiety becomes predominantly positively charged. As discussed below, a lipid having an imidazole moiety was prepared and used in preparation of liposomes.

Other suitable Z moieties include, for example, aromatic amines, aniline, aminosugars, and exemplary lipid structures described below.

In another embodiment, Z is a moiety having a pK value between about 4.5 to about 7.0, more preferably between about 4.8 to about 6.5, and most preferably between about 5.0 to about 6.0.

The lipids of the invention include a neutral linkage, L, joining the Z moiety and the tail portion of the lipid. Linkage L can vary, but in one embodiment is selected from a carbamate, and ester, and amide, a carbonate, a urea, an amine, and an ether. In a preferred prepared lipid, a carbamate linkage is emplyoed, wherein L is —X—(C=O)—Y—, X is NH, and Y is oxygen.

In the tail portion of the lipid, $R^1$ and $R^2$ are the same or different. $R^1$ and $R^2$ can be an unbranched alkyl or alkenyl chain having between about 8 to about 24 carbon atoms. Preferably, the $R^1$ and $R^2$ groups are between about 12 to about 22 carbon atoms in length, with $R^1=R^2=C_{17}H_{35}$ (such that the group is a stearyl group), and $R^1=R^2=C_{17}H_{33}$ (such that the group is an oleoyl group).

Figure 1:
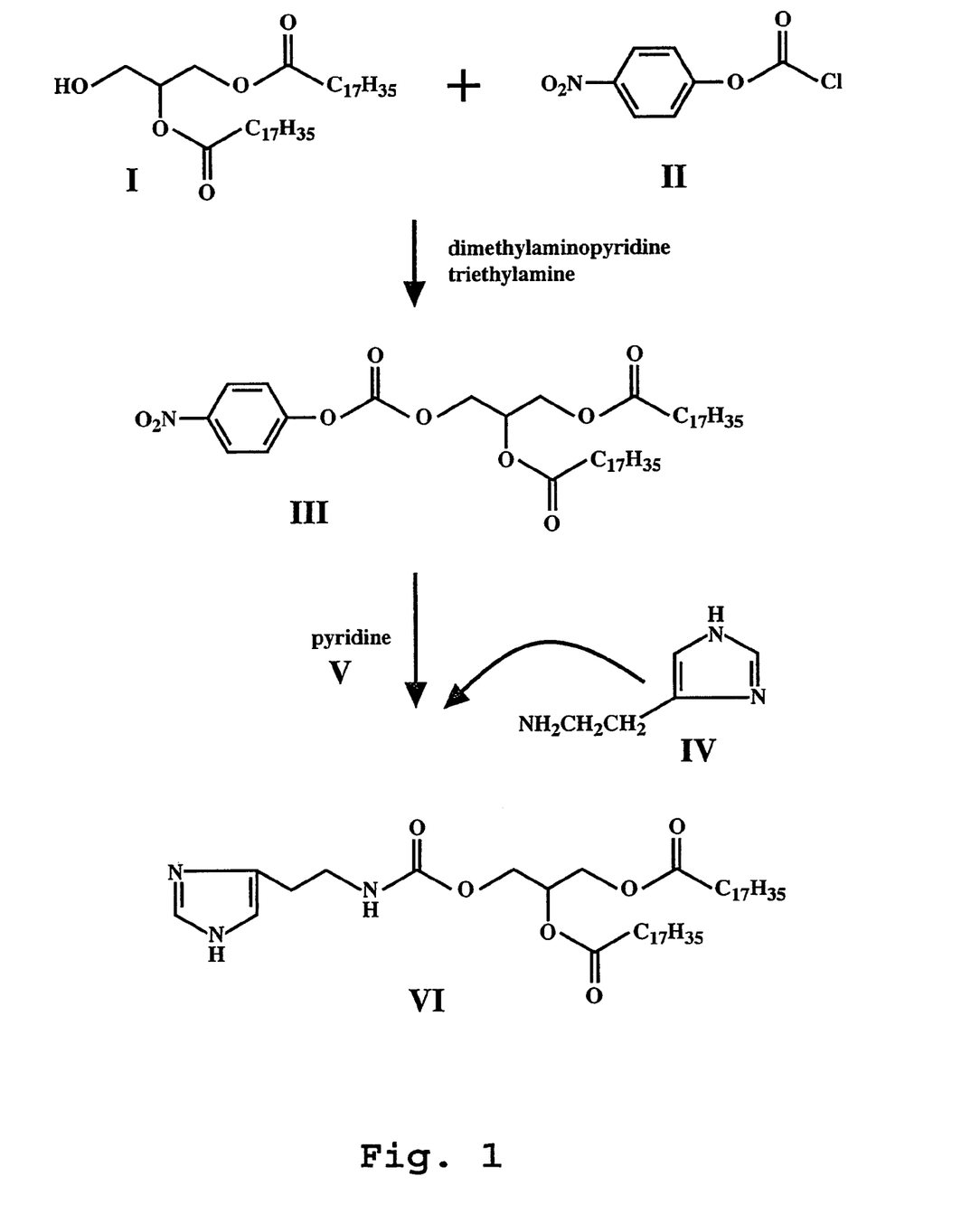
FIG. 1 shows a synthetic scheme for preparation of a lipid having a carbamate linkage and an imidazole Z group.

The lipid of the invention can be prepared using standard synthetic methods. A lipid was prepared having the structure shown above, wherein Z is an imidazole, n=2, L is a carbamate, and $R^1=R^2=C_{17}H_{35}$. A reaction scheme for preparation of this lipid is shown in FIG. 1. Full details of the synthesis are also provided in Example 1. Briefly, the para-nitrophenyl carbonate of 1,2-distearoyl glycerol (Compound I) and paranitrophenyl chloroformate (Compound II) and reacted with histamine (Compound IV), to yield a lipid (compound VI) having an imidazole moiety linked to a distearoyl tail via a carbamate linkage. A similar synthesis, using glycerol in place of 1-amino-2,3-propanediol, can also be used to produce a carbonat-linked product (L=—O—(C=O)—O—CH$_2$— or —O—(C=O)—CH$_2$—).

Figure 2A:
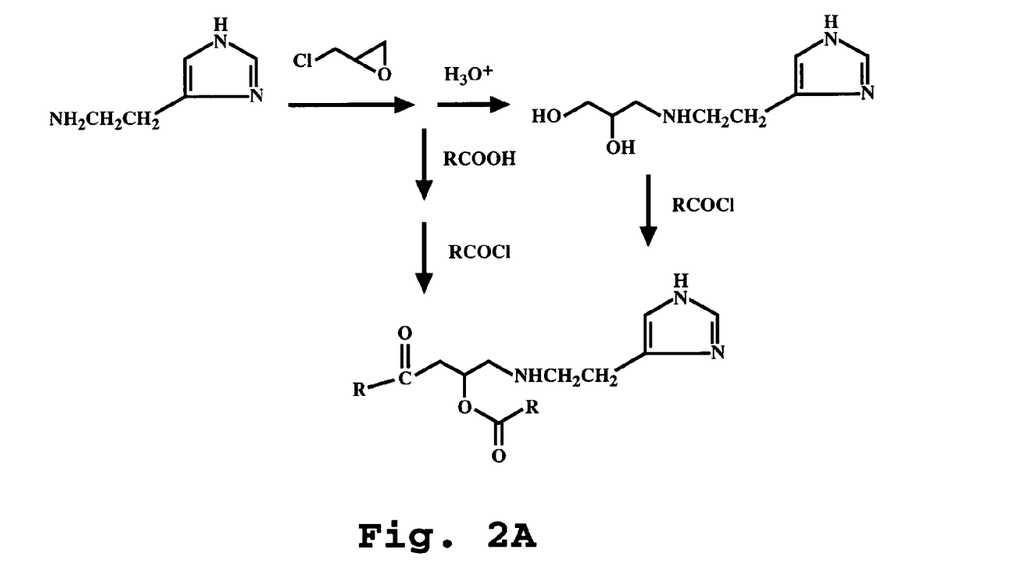
FIGS. 2A–2D show synthetic reaction schemes for preparation of pH responsive lipids.
Figure 2B:
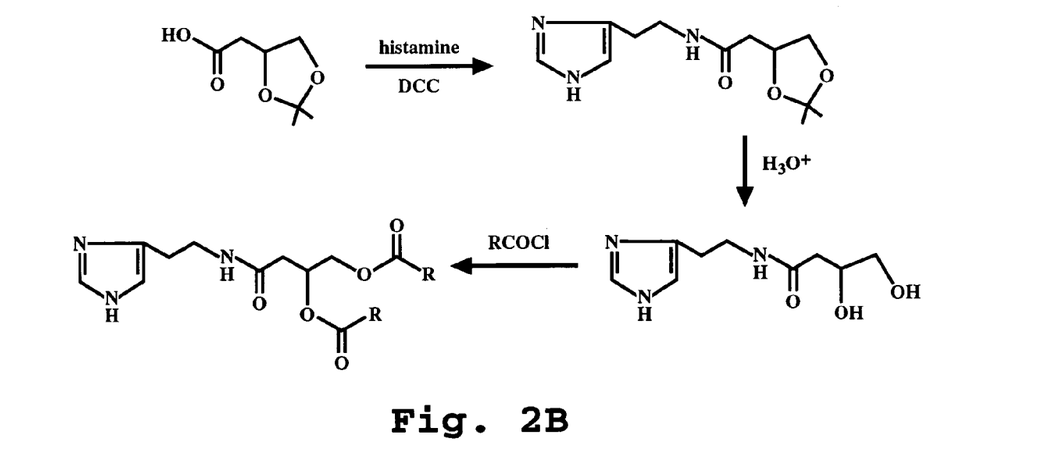

Given the guidance and examples herein, other synthesis of a lipid having other linkages can be readily accomplished by those of skill in the art. Other linkage include, for example, ether (L=O—CH$_2$—) and ester linkages (L=—O—(C=O)—), as well as urea amide, and amine linkages (i.e., where L=—NH—(C=O)—NH—, —NH—(C=O)—, or —NH—). A keto linkage, where X is a direct bond, may also be prepared. FIGS. 2A–2B illustrate preparation of an amine-linked lipid (FIG. 2A) and lipid having an NH-containing linkage (FIG. 2B), respectively. In FIG. 2A, the terminal amine of histamine is reacted with glycidyl chloride, hydrolyzing the resulting epoxide and acylation the resulting diol.

In FIG. 2B, lipid having an NH— containing linkage is prepared, for example, by reacting histamine with an activated derivative of glyceric acid acetonide (2,2-dimethyl-1,3-dioxolane-4-carboxylic acid) or the four-carbon homolog, 2,2-dimethyl-1,3-dioxolane-4-acetic acid. The diol is subsequently deprotected and acylated.

Figure 2C:
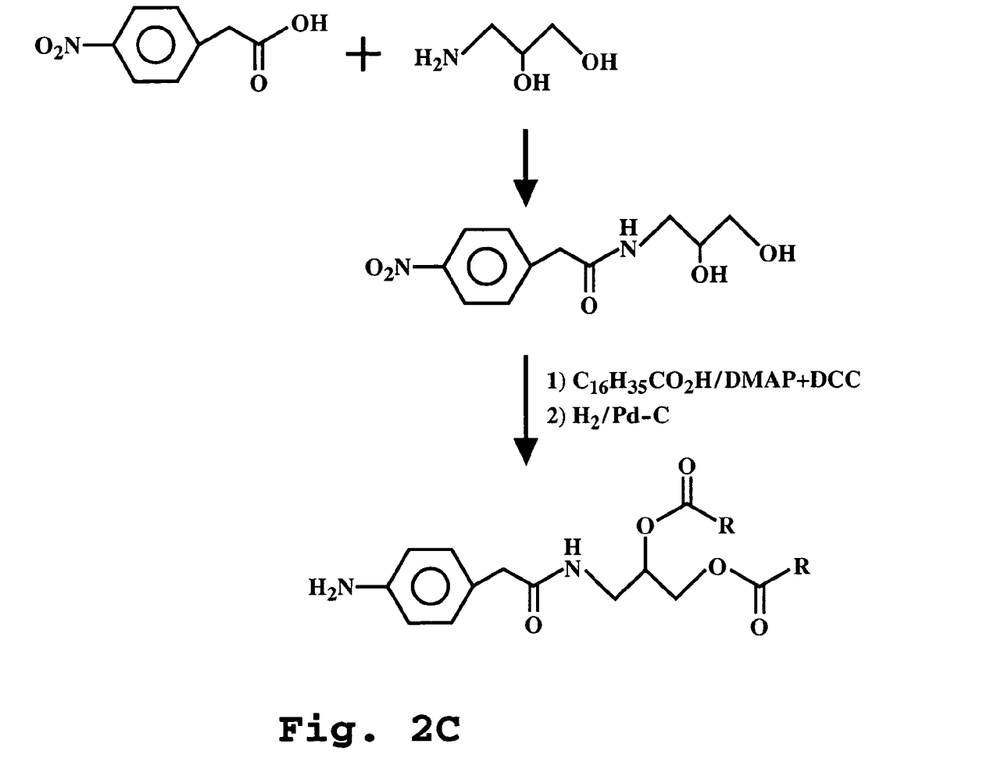
Figure 2D:
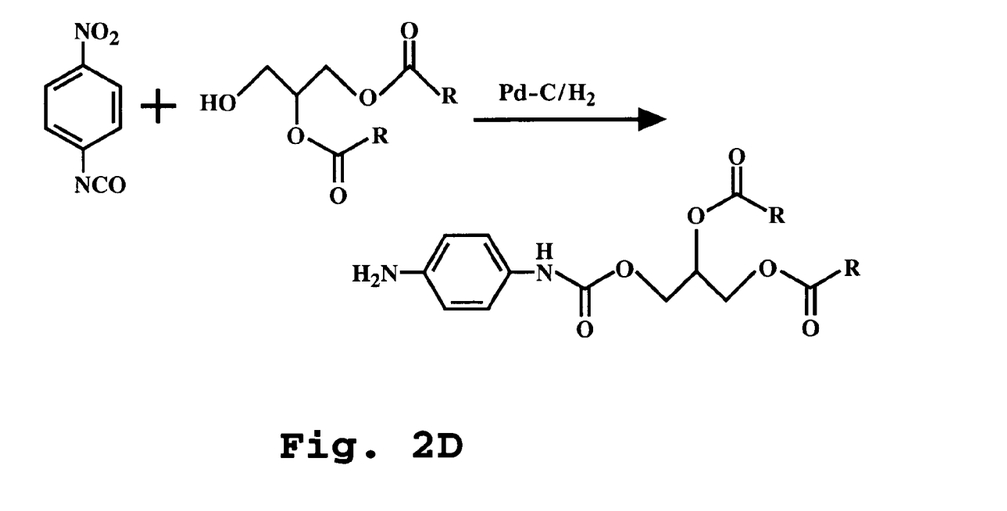

FIGS. 2C and 2D show additional reaction schemes for the preparation of pH responsive lipids according to the present invention.

Figure 3A:
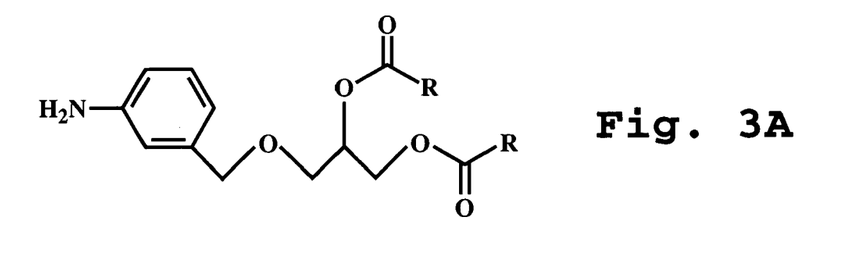
FIGS. 3A–3D show various structures of pH responsive lipids.
Figure 3B:
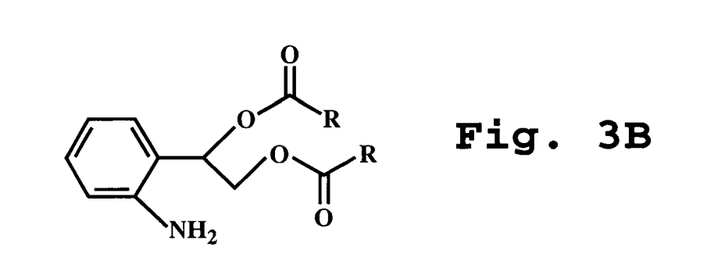
Figure 3C:
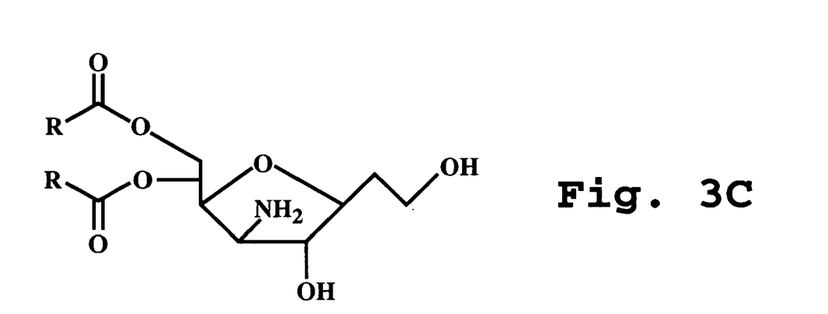
Figure 3D:
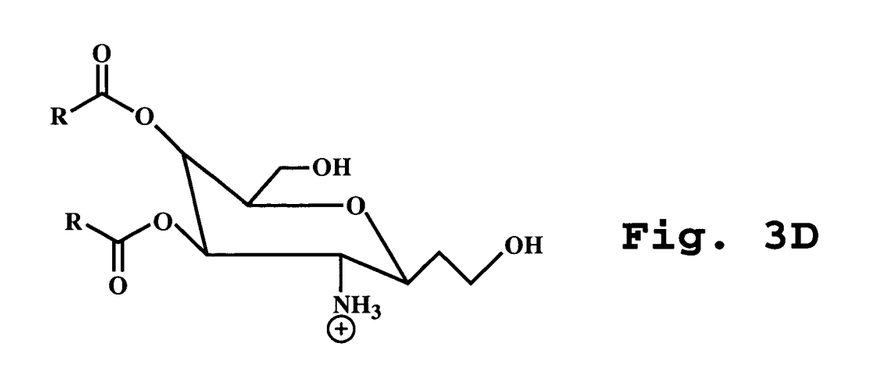

FIGS. 3A–3D show various structures of pH responsive lipids, wherein FIGS. 3A–3B show lipids having an aromatic amine as the "Z" moiety. FIGS. 3C–3D show lipids having an aminosugar attached to a lipid.

III. Liposome Composition

A. Liposome Components

Liposomes containing the lipid described above can be prepared by a variety of techniques, such as those described in Szoka et al., *Ann. Rev. Biophys. Bioeng.*, 9:467 (1980), and specific examples of liposomes prepared described fully below. Typically, the liposomes are multilamellar vesicles (MLVs), which can be formed by simple lipid-film hydration techniques. In this procedure, a mixture of liposome-forming lipids, of the type detailed below, are dissolved in a suitable organic solvent which is then evaporated in a vessel to form a thin film. The lipid film is subsequently covered by an aqueous medium, hydrating to form MLVs, typically with sizes between about 0.1 to about 10 microns.

Liposomes prepared in the present invention include, for example, liposomes having between about 1 to about 80 mole percent of the lipid and the structure given above. In preferred embodiments, liposomes include between about 5 to about 50 mole percent of the lipid. The remainder of the liposome lipid components can further include, for example, a variety of vesicle-forming lipids, i.e., lipids that form spontaneously into bilayer vesicles in water, as exemplified by the phospholipids. The vesicle-forming lipids of this type are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidylglycerol, phosphatidylserine, phosphatidic acid, phosphatidylinositol, and sphingomyelin, where the two hydrocarbon chains are typically between about 12 to about 22 carbon atoms in length, and have varying degrees of unsaturation.

The liposomes can further include a lipid that is stably incorporated into the liposome lipid bilayer, such as diacylglycerols, lyso-phospholipids, fatty acids, glycolipids, cerebrosides and sterols, such as cholesterol.

In one embodiment, liposomes of the invention include a surface coating of a hydrophilic polymer chain. "Surface-coating," as used herein, refers to the coating of a hydrophilic polymer on the surface of liposomes. The hydrophilic polymer is included in the liposome by including in a liposome composition one or more vesicle-forming lipids derivatized with a hydrophilic polymer chain. Liposomes having such a coating are known in the art, and have been described, for example, in U.S. Pat. No. 5,013,556. The surface coating of hydrophilic polymer chains is effective to increase the in vivo blood circulation lifetime of the liposomes when compared to liposomes lacking such a coating.

Vesicle-forming lipids suitable for derivatization with a hydrophilic polymer include, for example, any of the lipids listed above, and, in particular phospholipids, such as distearoyl phosphatidylethanolamine (DSPE).

Hydrophilic polymers suitable for derivatization with a vesicle-forming lipid include, for example, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, polyaspartamide and hydrophilic peptide sequences. The polymers may be employed as homopolymers or as block or random copolymers.

A preferred hydrophilic polymer chain is polyethyleneglycol (PEG), preferably having a molecular weight between about 500 to about 10,000 daltons, more preferably between about 1,000 to about 5,000 daltons. Methoxy or ethoxy-capped analogues of PEG are also preferred hydrophilic polymers. These polymers are commercially available in a variety of polymer sizes, for example, between about 120 to about 20,000 daltons.

Preparation of vesicle-forming lipids derivatized with hydrophilic polymers has been described, for example, in U.S. Pat. No. 5,395,619, and in Zalipsky STEALTH LIPO-SOMES, (D. Lasic and F. Martin, Eds., CRC Press, Chapter 9 (1995)).

Liposomes having such a coating preferably contain between about 1 to about 20 mole percent of the derivatized lipid with the remaining liposome forming components, e.g., vesicle-forming lipids. Exemplary methods of preparing derivatized lipids and of forming polymer-coated liposomes have been described in co-owned U.S. Pat. Nos. 5,013,556, 5,631,018 and 5,395,619. The hydrophilic polymer may be stably coupled to the lipid, or coupled through an unstable linkage that allows the coated liposomes to shed the coating of polymer chains as they circulate in the bloodstream or in response to a stimulus.

The liposomes may also include an entrapped agent, where the term "entrapped" includes encapsulation of an agent in the aqueous core and aqueous spaces of liposomes, as well as entrapment of an agent in the lipid bilayer(s) of the liposomes.

Agents useful in the composition of the invention are widely varied, and include, for example, agents for therapeutic applications as well as diagnostic applications. The selected therapeutic or diagnostic agent can be incorporated into liposomes by standard methods, including: (i) passive entrapment of a water-soluble compound by hydrating a lipid film with an aqueous solution of the agent; (ii) passive entrapment of a lipophilic compound by hydrating a lipid film containing the agent; and (iii) loading an ionizable drug against an inside/outside liposome pH gradient. Other suitable methods include reverse evaporation phase liposome preparation.

In a preferred embodiment, the liposomes include a nucleic acid, selected from a variety of DNA and RNA based nucleic acids, including fragments, i.e., truncations, mutations, and analogues thereof. A variety of genes for treatment of various conditions has been described in the art, and coding sequences and/or ORFs for specific genes of interest can be readily retrieved from DNA databanks, such as GenBank or EMBL. For example, polynucleotides for treatment of viral, malignant and inflammatory diseases and conditions, such as, cystic fibrosis, adenosine deaminase deficiency, and AIDS, have been described. Treatment of cancers by administration of tumor suppressor genes, such as APC, DPC4, NF-1, NF-2, MTS1, RB, p53, WT1, BRCA1, BRCA2, and VHL are contemplated.

Examples of specific nucleic acids for treatment of a specific condition include, for example: HLA-B7, tumors, colorectal carcinoma, melanoma; IL-2, cancers, especially breast cancer, lung cancer, and tumors; IL-4, cancer; TNF, cancer; IGF-1 antisense, brain tumors; IFN, neuroblastoma; GM-CSF, renal cell carcinoma; MDR-1, cancer, especially advanced cancer, breast and ovarian cancers; and HSV thymidine kinase, brain tumors, head and neck tumors, mesothelioma, ovarian cancer.

Nucleic acids of the invention can be "antisense nucleic acids" composed of sequences complementary to their target, typically a messenger RNA (mRNA) or an mRNA precursor. The mRNA typically contains genetic information in the functional, or sense orientation, and binding of the antisense polynucleotide may inactivate the intended mRNA and prevent translation to protein. Such antisense nucleic acids are determined based on biochemical experiments showing that proteins are translated from specific RNAs. Once the sequence of the RNA is known, an antisense nucleic acid that will bind to the RNA through complementary Watson-Crick base pairs can be designed. Such antisense nucleic acids typically contain between about 10 to about 40 base pairs, more preferably between about 10 to about 25 base pairs, and most preferably between about 15 to about 20 base pairs.

The antisense nucleic acid can be modified for improved resistance to nuclease hydrolysis. Such analogues include, for example, phosphorothioate, methylphosphonate, phosphodiester, and p-ethoxy oligonucleotides (see, for example, WO 97/07784). The entrapped agent can also be a ribozyme or catalytic RNA.

The nucleic acid may also be inserted into a plasmid or vector, preferably one that is a circularized or closed double-stranded molecule having sizes preferably in the 5–40 Kbp (kilo basepair) range. Such plasmids or vectors are constructed according to well-known methods and include a therapeutic nucleic acid or gene, i.e., the gene or nucleic acid to be expressed in gene therapy, under the control of a suitable promoter and enhancer, and other elements necessary for replication within the host cell and/or integration into the host-cell genome. Methods for preparing plasmids and vectors useful for gene therapy are widely known and referenced in the art.

Nucleic acids, such as a DNA plasmid, can be entrapped in a liposome by passive entrapment during hydration of the liposome lipid film. Other procedures for entrapping nucleic acids include, for example, condensing the nucleic acid in a single-molecule form, wherein the nucleic acid is suspended in an aqueous medium containing agents such as protamine sulfate, spermine, spermidine, histone, lysine, or mixtures thereof, or other suitable polycationic condensing agent, under conditions that are effective to condense the nucleic acid into small particles. The solution of condensed nucleic acid molecules is used to rehydrate a dried lipid film to form liposomes with the condensed nucleic acid in entrapped form.

In another embodiment, liposomes may be prepared to contain surface groups, such as antibodies or antibody fragments, small effector molecules for interacting with cell-surface receptors, antigens, and other like compounds for achieving desired target-binding properties to specific cell populations. Such ligands can be introduced in the liposomes by including in the liposomal lipids a lipid derivatized with the targeting molecule, or a lipid having a polar-head chemical group that can be derivatized with the targeting molecule in preformed liposomes.

Lipids can be derivatized with a targeting ligand by covalently attaching the ligand to the free distal end of a hydrophilic polymer chain, which is attached at its proximal end to a vesicle-forming lipid. There is a wide variety of techniques for attaching a selected hydrophilic polymer to a selected lipid and activating the free, unattached end of the polymer for reaction with a selected ligand. In particular, the hydrophilic polymer PEG has been widely studied (Allen, T. M., et al., Biochemicia et Biophysica Acta 1237:99–108 (1995); Zalipsky, S., Bioconjugate Chem., 4(4):296–299 (1993); Zalipsky, S., et al., FEBS Lett. 353:71–74 (1994); Zalipsky, S., et al., Bioconjugate Chemistry, 705–708 (1995); Zalipsky, S., in STEALTH LIPOSOMES (D. Lasic and F. Martin, Eds.) Chapter 9, CRC Press, Boca Raton, Fla. (1995)).

Targeting ligands are well known to those of skill in the art, and in a preferred embodiment, the targeting ligand is one that has binding affinity to endothelial tumor cells, and is preferably internalized by the cells. Such ligands often bind to an extracellular domain of a growth factor receptor. Exemplary receptors include the c-erbB-2 protein product of the HER2/neu oncogene, epidermal growth factor (EGF) receptor, basic fibroblast growth receptor (basic FGF) receptor and vascular endothelial growth factor receptor, E-, L- and P-selectin receptors, folate receptor, CD4 receptor, CD19 receptor, αβ integrin receptors, and chemokine receptors.

According to the invention, prepared liposomes can be sized to have substantially homogeneous sizes in a selected size range, typically between about 0.01 to about 0.5 microns, more preferably between about 0.03 to about 0.40 microns. One effective sizing method for REVs and MLVs involves extruding an aqueous suspension of the liposomes through a series of polycarbonate membranes having a selected uniform pore size in the range of about 0.03 to about 0.20 micron, typically about 0.05, 0.08, 0.10, or 0.20 microns. The pore size of the membrane corresponds approximately to the largest sizes of liposomes produced by extrusion through that membrane, particularly where the preparation is extruded two or more times through the same membrane. Homogenization methods are also useful for down-sizing liposomes to sizes of 100 nm or less (Martin, F. J., in *SPECIALIZED DRUG DELIVERY SYSTEMS-MANUFACTURING AND PRODUCTION TECHNOLOGY*, (P. Tyle, Ed.) Marcel Dekker, New York, pp. 267–316 (1990)).

B. Preparation and Characterization of Exemplary Compositions

Liposomes, described in Example 1, having an imidazole moiety linked to a distearoyl tail via a carbamate linkage were prepared as described in Example 2. The liposomes were composed of 60 mole percent partially hydrogenated soy-bean phosphatidylcholine (PHSPC), and 40 mole percent of the imidazole-carbamate-distearoyl lipid. The liposomes in the composition had an average particle size of 80 nanometers (nm) after sonication.

Figure 4:
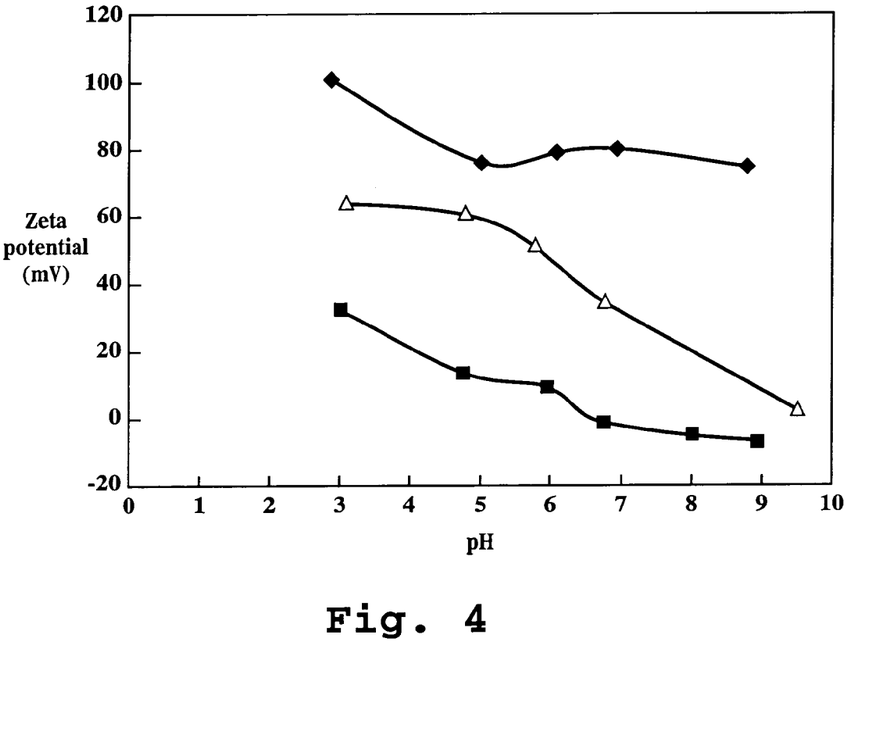
FIG. 4 is a graph showing the zeta potential, in mV, as a function of media pH for liposomes prepared with the lipid of the invention (open triangles), a cationic lipid (closed diamonds) and a neutral lipid (closed squares)

The zeta potential of these liposomes was measured as a function of pH, and the results are shown in FIG. 4 (open triangles). For comparison, two liposome compositions not containing the lipid of the invention were prepared. One composition included a cationic lipid, whereas the other composition consisted of a single neutral lipid, PHSPC. The cationic liposome composition was composed of 55 mole percent of dimethyldioctadecylammonium (DDAB) and 45 mole percent of cholesterol.

The zeta potential values provide a measure of the apparent charge on the outer surface of the liposomes. More specifically, the zeta potential is a measure of the potential that arises across the interface between a liquid boundary layer in contact with a solid and the movable diffuse layer in the body of the liquid, e.g., the slipping plane. Zeta potential values were measured as set forth in the methods section below, using a commercially available apparatus.

In FIG. 4, a liposome prepared with the imidazole-carbamate-distearoyl lipid (open triangles) showed a strong relationship between zeta potential and pH of the surrounding media. As observed, at pH values of less than about 5.0, the zeta potential was relatively constant at about 65 millivolts (mV). As the pH of the media increased, the zeta potential decreased rapidly. In contrast, cationic liposomes (e.g., liposomes of DDAB-cholesterol, solid diamonds), and the neutral liposome formulation (solid squares) had less change in zeta potential as the pH of the suspension media increased.

The rapid change in zeta potential of the liposomes containing imidazole-carbamate-distearoyl lipids as the pH of the suspension media, increased due to the pK property of the imidazole moiety. The pK of imidazole is about pH 6.0. At pH less than 6.0, the imidazole moiety is predominately, e.g., greater than 50%, positive in charge, and the zeta potential of the imidazole-carbamate-distearoyl lipid-containing liposomes tends to positive. At pH higher than 6.0, imidazole turns to neutral charge, e.g., greater than 50% neutral, and the positive zeta potential of the imidazole-carbamate-distearoyl lipid-containing liposomes decreases, or tends to neutral.

In another experiment, liposomes were prepared that included the imidazole-carbamate-distearoyl lipid (prepared as described in Example 1), and contained entrapped DNA. As described in Example 3A, condensed plasmid DNA was contacted with liposomes containing a 60/40 molar ratio of PHSPC and the imidazole-carbamate-distearoyl lipid. The pH of the liposome solution was adjusted to about 4.0 prior to contact with the condensed DNA. At a pH of about 4.0, the imidazole head group on the lipid is positively charged such that the negatively charged DNA becomes electrostatically bound to the lipid. With continuous stirring, the liposomes form around the DNA entrapping the DNA within the lipid bilayer. Accordingly, the invention provides a method for efficiently entrapping a negatively-charged agent by preparing liposomes with a pH-responsive lipid and contacting the agent with the liposomes under conditions wherein the pH-responsive lipid tends toward positive charge.

Liposomes having entrapped DNA were compared with a sample containing only DNA. These two samples were treated with DNase I for 30 minutes (see Example 3B). After the treatment period, an aliquot of each sample was loaded onto an agarose gel containing ethidium bromide and electrophoresed. Samples of the same liposomes and of DNA not treated with DNase I were also loaded onto the agarose gel.

Figure 5:
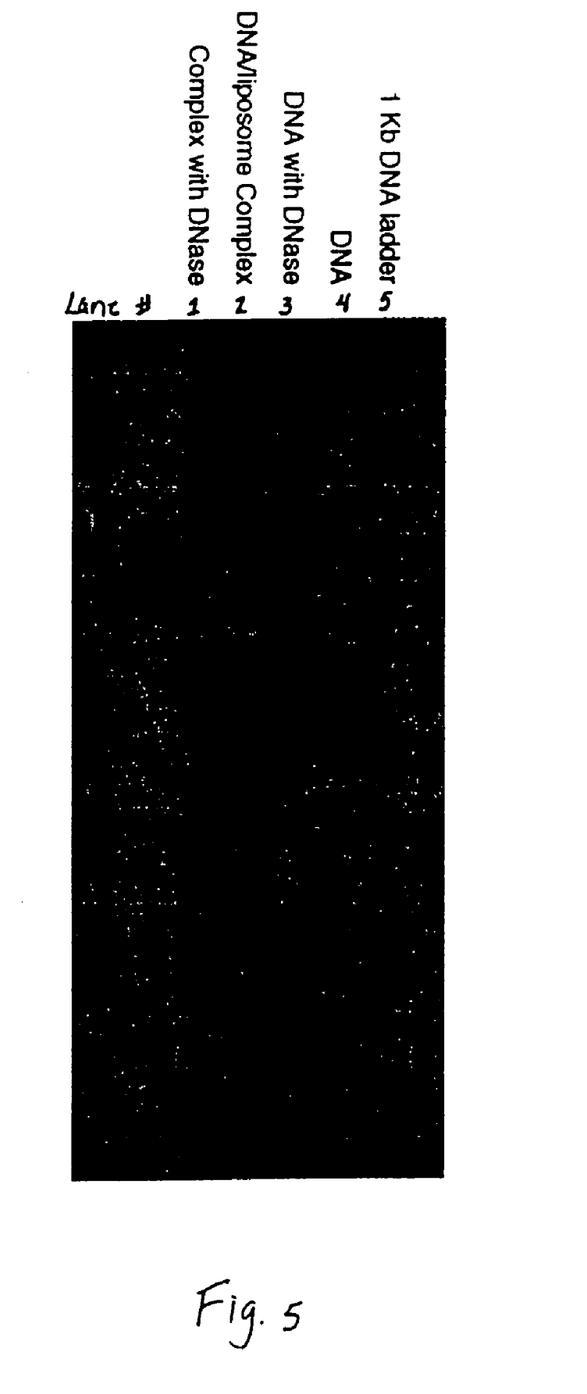
FIG. 5 is a micrograph of gel electrophoresis assay of liposomes prepared with the pH-responsive lipid of the invention having entrapped DNA, where the liposomes were exposed to DNAse I for 30 minutes (Lane 1); liposomes prepared with the pH-responsive lipid of the invention having entrapped DNA (Lane 2); DNA exposed to DNAse I for 30 minutes (Lane 3); DNA (Lane 4); and 1 kB DNA ladder standard (Lane 5)

FIG. 5 is a micrograph of the gel electrophoresis assay of these samples.

Lane 1 is the DNase-treated liposomes; Lane 2 is the liposomes (not treated with DNase I); Lane 3 is the DNA treated with DNase I; Lane 4 is the DNA; and Lane 5 is a 1 kB DNA ladder standard.

FIG. 5 shows that DNA entrapped in the liposomes was protected from digestion by the DNase I, (by comparing Lane 1 with Lane 3, where DNA alone was digested by the DNase I).

In another study, liposomes including a pH responsive lipid and a targeting antibody were prepared. These liposomes were used for in vitro transfection of human lung tumor cells.

Specifically, a DNA reporter plasmid vector pEGFP-C1 (Clontech, Palo Alto Calif.) containing green fluorescence protein gene was entrapped in liposomes according to the procedure of Example 3A. The ratio of total lipids to DNA in the liposomes was about 14 nanomole lipids per 1 microgram ($\mu$g) DNA. After the DNA was entrapped in the liposomes, an anti-integrin antibody 1 F11 Fab' was inserted into the lipid bilayer by incubating the liposomes with micelles of 1 F11-Fab'-conjugated to polyethyleneglycol-DSPE (PEG-DSPE). The 1 F11-Fab'-PEG-DSPE conjugate was prepared using conventional technology by attaching the antibody at the N-terminal maleimide of PEG-DSPE, as described, for example, in Zalipsky, *STEALTH LIPOSOMES*, (D. Lasic and F. Martin, Eds., CRC Press, Chapter 9 (1995)). The antibody-containing micelles and the liposomes were incubated overnight at room temperature.

Human lung tumor cell line 2E9, having an integrin receptor, were incubated with the liposomes in vitro. Liposomes containing the 1 F11-PEG-DSPE conjugate and control liposomes lacking antibody (containing PDG-DSPE absent the antibody) were incubated with the cells at a concentration of 5 $\mu$g DNA/70 nmole lipid per ml for 4 hours at 37° C. After the incubation period, the medium was changed to remove the liposomes.

Figure 6:
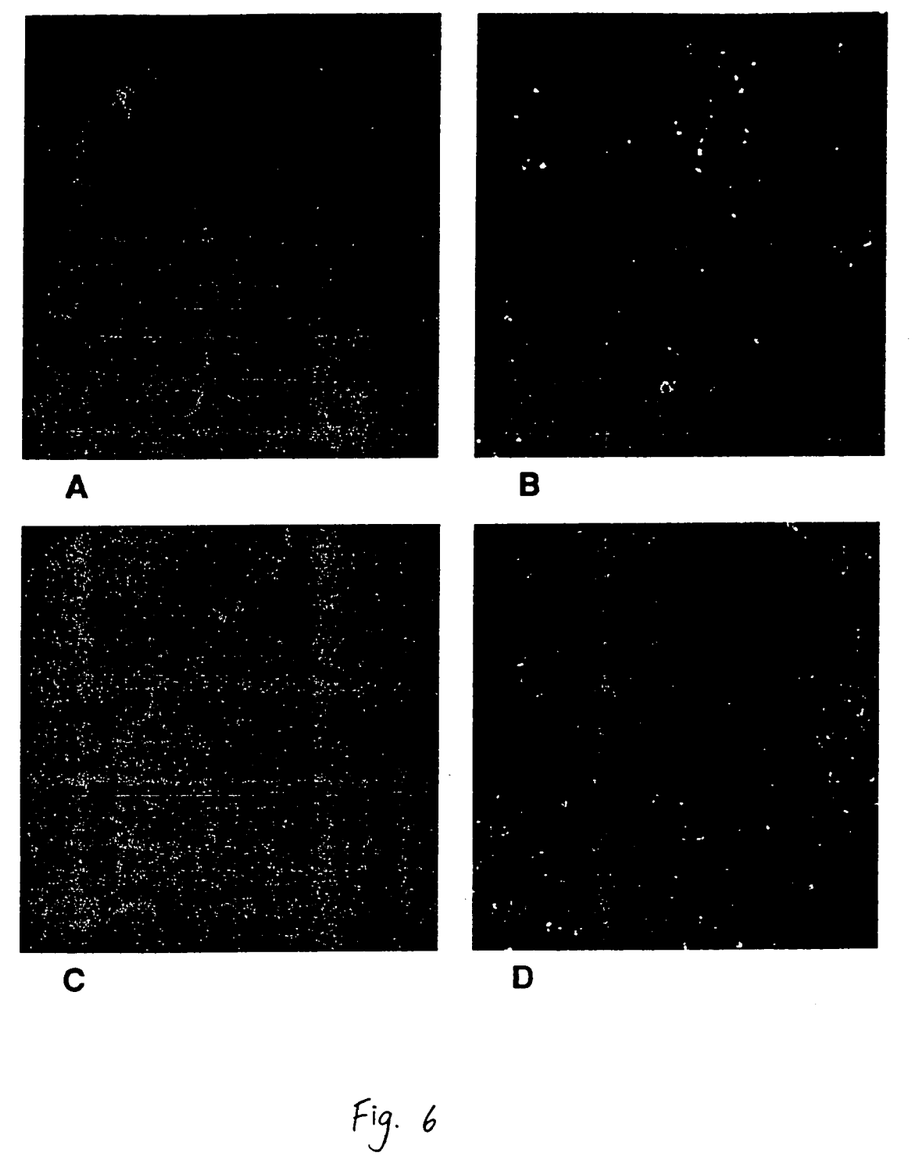
FIGS. 6A–6D are images of micrographs of human lung tumor cells in vitro after transfection with liposomes prepared with the pH-responsive lipid of the invention and a targeting antibody. The liposomes include an entrapped plasmid encoding for green fluorescence protein, where

Green fluorescence was examined 24 hours after transfection, and the results are shown in FIGS. 6A–6D. FIGS. 6A–6B are micrographs for the cells transfected with the 1 F11-conjugated liposomes. FIG. 6A shows the cells viewed under fluorescence microscopy and FIG. 6B shows the cells viewed under light microscopy. FIG. 6A shows that the cells were transfected, as evidenced by the light regions, which correspond to fluorescing cells. FIGS. 6C–6D are images of the cells transfected with the control formulation lacking targeting antibody. No transfection occurred, as evidenced by the lack of fluorescence when the cells were viewed by fluorescence microscopy (FIG. 6C).

The lipid of the invention includes a moiety that is responsive to pH such that at a pH of about 7.4 the lipid is essentially neutral. Thus, liposomes when administered to a subject, such as a mammal, for example, a human, are uncharged, which allows for a longer blood circulation time than achieved with charged liposomes. Liposomes that are endocytosed or that reach a specific in vivo region where the pH is lower, become charged as the lipid becomes positively charged. This is due to the liposomes having a pH responsive moiety. This can occur, for example, in a tumor region or in a lysosyme. Thus, a lipid having an imidazole moiety, which has a pK of about 6.0, will become predominantly positively charged at pH values less than 6.0. Therefore, in an endosome where the pH is between about 5.0 to about 6.0, the lipid protenates, facilitating uptake and release of the entrapped DNA into the cytoplasm of the cell (Xu and Szoka, *Biochemistry*, 35:5616–5623 (1996)). Further illustration of this principle is set forth in the Examples below.

EXAMPLES

The following examples are illustrative of the invention.

Materials: The following materials were obtained from the indicated source: partially hydrogenated soy phosphatidylcholine (Vernon Walden Inc., Green Village, N.J.); cholesterol (Solvay Pharmaceuticals, The Netherlands); dioleoylphosphatidyl ethanolamine (DOPE) and dimethyldioctadecylammonium (DDAB) (Avanti Polar Lipids, Inc., Birmingham, Ala.).

Methods: Dynamic light scattering was performed using a Coulter N4-MD (Coulter, Miami Fla.).

Zeta-Potential: Zeta potential was measured using a ZETASIZER 2000 from Malver Instruments, Inc. (Southborough Mass.). The instrument was operated as follows: number of measurements: 3; delay between measurements: 5 seconds; temperature: 25 C; viscosity: 0.89 cP; dielectric constant: 79; cell type: capillary flow; zeta limits: −150 mV to 150 mV.

Example 1

Preparation of Exemplary Lipid

A. Preparation of para-nitrophenyl carbonate of distearoyl glycerol

As illustrated in FIG. 1, 1,2-distearoyl-sn-glycerol (500 mg, 0.8 mmol: Compound I) was dried azeotropically with benzene (3 times with rotary evaporator). Para-nitrophenyl chloroformate (242 mg, 1.2 mmol, 1.5 eq; Compound II), 4-dimethylaminopyridine (10 mg, 0.08 mmol, 0.1 eq), and triethylamine (334 µl, 204 mmol, 3 eq) were added to 1,2-distearoyl glycerol in $CHCl_3$ (5 ml). The reaction mixture was stirred at room temp for 2 h. TLC showed that the reaction was complete. The mixture was diluted with $CHCl_3$ (50 ml) and extracted with 10% citric acid (3×16 mL). The organic layer was dried ($MgSO_4$) and evaporated to give a solid. The solid (light orange) was washed with acetonitrile (4×3 mL) to remove excess of p-nitrophenyl chloroformate. The product, para-nitrophenyl carbonate of distearoyl glycerol (Compound III), was dried under vacuum over $P_2O_5$. Yield: 557 mg (88%). $^1$H NMR (360 MHz, DMSO-D6): δ 0.88 (t, $CH_3$, 6H); 1.26 (s, $CH_2$ 58H); 1.62 (m, $CH_2CH_2CO$, 4H); 2.4 (2xt, $CH_2CO$, 4H); 4.2 (dd, trans $CH_2OCO$, 1H): 4.35 (m, $CH_2OCOO$, 2H); 4.5 (dd, cis $CH_2OCO$, 1H); 5.38 (m, $CH_2CHCH_2$, 1H); 7.4 (d, $C_6H_5$, 2H); 8.3 (d, $C_6H_5$, 2H).

B. Preparation of Carbamate of Histamine and Distearoyl Glycerol

Para-nitrophenyl carbonate of 1,2-distearoyl glycerol (350 mg, 0.44 mmol, Compound III) was added to Histamine (46 mg, 0.40 mmol, 0.9 eq; Compound IV) in $CHCl_3$ (1 ml) with DMSO (200 µl). Pyridine (300 µl; Compound V) was added to the solution. The reaction mixture was stirred at room temperature overnight for about 20 hours. TLC ($CHCl_3$: MeOH=90:10) showed that the reaction was complete. Solvent was evaporated. The product (Compound VI) was dissolved in $CHCl_3$, poured on to silica gel (Aldrich, 230–400 mesh, 60 Å) column, and eluted with the following solvents, $CHCl_3$: $CH_3COCH_3$=90:10, 40 ml (upper spot eluted); $CHCl_3$: IPA=80:20, 40 ml (product eluted); $CHCl_3$: IPA=70:30, 40 ml (more product eluted). Fractions containing pure product were combined, and evaporated. The product was dried under vacuo over $P_2O_5$ and was obtained as white solid (236 mg, 80% yield). $^1$H NMR (360 MHZ, $CDCl_3$/MeOH=1:1 with TMS):δ 0.88 (t, CH3, 6H); 1.28 (s, $CH_2$, 56H; 1.62 (m, $CH_2CH_2CO$, 4H); 2.34 (2xt, $CH_2CO$, 4H); 2.77 (t, $CH_2CH_2NH$, 2H); 3.18 (t, $CH_2CH_2CO$, 2H); 4.05–4.2 (dd, cis and trans $CH_2CHCH_2$, 4H); 5.13 (m, $CH_2CHCH_2$, 1H); 608 (s, Histamine, 1H); 7.53 (s, Histamine, 1H).

Example 2

Placebo Liposome Preparation

The lipid (Compound VI) prepared as described in Example 1 and partially hydrogenated soy phosphatidylcholine (PHSPC) in a molar ratio of 40/60 were dissolved in chloroform and/or methanol in a round bottom flask. The solvents were removed by rotary evaporation, and the dried lipid film produced was hydrated with deionized to produce large multilamellar vesicles.

Comparative liposome formulations were prepared using 100 mole percent PHSPC and with a 40/60 molar ratio of DDAB-cholesterol by a similar methodology.

The liposome size of each formulation was determined by dynamic light scattering.

Example 3

Preparation of Liposomes Containing Nucleic Acid

A. Preparation of Liposomes with Entrapped DNA

Complexes were prepared at room temperature as follows. First, 400 µg luciferase reporter plasmid DNA was condensed in 5% glucose solution by adding 100 µg histone with slow, continuous stirring for 10 minutes.

A solution of PHSPC and the pH responsive lipid prepared in Example 1 (Compound VI) in a molar ratio of 40/60 at a total lipid amount of 12,000 nm in 5% glucose was adjusted to pH=4. The condensed DNA solution was added to the acidic liposome solution slowly with continuous stirring for 10 minutes. The final concentration of DNA was 0.25 mg/ml and the total lipid concentration was 7.5 mM. The ratio of DNA total lipids was 1 µg DNA to 30 nmole lipids.

B. DNase I Assay

DNA alone and DNA entrapped in liposomes were treated with DNase I in the presence of 10 mM $MgSO_4$ at 37° C. for 30 minutes. After treatment, the liposome/DNase mixture was extracted with phenol/$CHCl_3$ and $CHCl_3$ to separate lipids and proteins from DNA.

Aliquots of the DNase treated-DNA and of the DNA fraction from the DNase-treated, liposomes having entrapped DNA were loaded onto a 1% agarose gel containing ethidium bromide and electrophoresed to examine the integrity of the DNA. As controls, DNA and liposomes not treated with DNAse were loaded onto the gel, along with a 1 Kb DNA standard. The results are shown in FIG. 5.

The complete disclosures of the patents, patent documents, publications, etc., cited herein are incorporated by reference in their entirety as if each were individually incorporated. Various modifications and alterations to this invention will become apparent to those skilled in the art without departing from the scope of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

It is claimed:

1. A liposome composition comprising:
a lipid having the formula wherein each of $R^1$ and $R^2$ is an alkyl or alkenyl chain having between about 8 to about 24 carbon atoms;
n=0-20;
L is selected from the group consisting of (i) —X—(C=O)—Y—, (ii) —X—(C=O)—, wherein X and Y are independently selected from oxygen, NH, and a direct bond, and (iii) —O—$CH_2$—; and
Z is a weakly basic moiety that has a pK of less than about 7.4 and greater than about 4.0.

2. The composition of claim 1, wherein X is NH and Y is oxygen.

3. The composition of claim 1, wherein L is a carbamate linkage, an ester linkage or a carbonate linkage.

4. The composition of claim 1, wherein L is NH—(C=O)—O—.

5. The composition of claim 1, wherein Z is an imidazole.

6. The composition of claim 1, comprising between about 1 to about 80 mole percent of the lipid.

7. The composition of claim 1, wherein Z is a moiety having a pK value between about 5.0 to about 6.5.

8. The composition of claim 1, wherein each of $R^1$ and $R^2$ is an unbranched alkyl or alkenyl chain having between about 8 to about 24 carbon atoms.

9. The composition of claim 8, wherein each of $R^1$ and $R^2$ is $C_{17}H_{35}$.

10. The composition of claim 1, wherein n is between 1-10.

11. The composition of claim 1, further comprising a therapeutic compound entrapped in the liposomes.

12. The composition of claim 11, wherein the therapeutic agent is a nucleic acid.

13. The composition of claim 12, wherein the nucleic acid is selected from the group consisting of DNA, RNA, and their complements.

14. The composition of claim 1, further comprising a ligand for targeting the liposomes to a target site.

15. The composition of claim 14, wherein the ligand has binding affinity for endothelial tumor cells and is internalized by the cells.

16. The composition of claim 15, wherein the ligand is selected from the group consisting of E-selectin, Her-2 and FGF.

17. The composition of claim 1, wherein said liposomes further comprise between about 5 to about 20 mmole percent of a vesicle-forming lipid derivatized with a hydrophilic polymer chain.

18. The composition of claim 17, wherein the hydrophilic polymer chain is polyethyleneglycol (PEG).

19. A method for delivering a therapeutic agent to a subject, comprising:
preparing liposomes comprising a lipid having the formula wherein each of $R^1$ and $R^2$ is an alkyl or alkenyl chain having between about 8 to about 24 carbon atoms;
n=0-20;
L is selected from the group consisting of (i) —X—(C=O)—Y—, (ii) —X—(C=O)—, wherein X and Y are independently selected from oxygen, NH, and a direct bond, and (iii) —O—$CH_2$—;
Z is a weakly basic moiety that has a pK of less than about 7.4 and greater than about 4.0; and
administering the liposomes to the subject.

20. The method of claim 19, wherein the preparing comprises entrapping a nucleic acid in the liposomes.

21. The method of claim 20, wherein the nucleic acid is DNA, RNA, or their complements.

22. The method of claim 19, wherein the preparing further comprises entrapping a protein or a protein fragment in the liposomes.

* * * * *